United States Patent
Gabbrielli et al.

(10) Patent No.: US 9,370,426 B2
(45) Date of Patent: Jun. 21, 2016

(54) RELATING TO JOINTS AND/OR IMPLANTS

(75) Inventors: Ruggero Gabbrielli, Trento (IT); Irene Gladys Turner, Bradford on Avon (GB); Christopher Rhys Bowen, Bath (GB); Emanuele Magalini, Trento (IT)

(73) Assignee: RENISHAW PLC, Wotton-under-Edge (GB)

( * ) Notice: Subject to any disclaimer, the term of this patent is extended or adjusted under 35 U.S.C. 154(b) by 0 days.

(21) Appl. No.: 12/994,666

(22) PCT Filed: Sep. 8, 2008

(86) PCT No.: PCT/GB2008/003027
§ 371 (c)(1),
(2), (4) Date: Feb. 7, 2011

(87) PCT Pub. No.: WO2009/144434
PCT Pub. Date: Dec. 3, 2009

(65) Prior Publication Data
US 2011/0125284 A1    May 26, 2011

(30) Foreign Application Priority Data
May 28, 2008 (GB) .................................. 0809721.4

(51) Int. Cl.
*A61F 2/34* (2006.01)
*A61F 2/30* (2006.01)
(Continued)

(52) U.S. Cl.
CPC ............ *A61F 2/30767* (2013.01); *B22F 7/004* (2013.01); *A61F 2/3094* (2013.01); *A61F 2/32* (2013.01); *A61F 2/36* (2013.01); *A61F 2/367* (2013.01); *A61F 2/3662* (2013.01); *A61F 2/3672* (2013.01); *A61F 2/3676* (2013.01); *A61F 2002/30011* (2013.01); *A61F 2002/30062* (2013.01); *A61F 2002/3092* (2013.01); *A61F 2002/30322* (2013.01); *A61F 2002/30838* (2013.01); *A61F 2002/30962* (2013.01); *A61F 2002/3611* (2013.01); *A61F 2210/0004* (2013.01); *A61F 2250/0023* (2013.01); *A61F 2250/0026* (2013.01); *A61F 2310/00011* (2013.01); *A61F 2310/00017* (2013.01);
(Continued)

(58) Field of Classification Search
USPC .......... 623/22.21–22.39, 23.29, 23.53–23.55, 623/23.72–23.76
See application file for complete search history.

(56) References Cited

U.S. PATENT DOCUMENTS 3,848,273 A * 11/1974 Frey ........................... 623/23.29
4,542,539 A *  9/1985 Rowe et al. ................ 623/23.57
(Continued)

OTHER PUBLICATIONS

International Search Report and Written Opinion of the International Searching Authority, International Application No. PCT/GB2008/003027, International Filing Date Sep. 8, 2008, Date of International Search Report Nov. 2, 2009.
(Continued)

*Primary Examiner* — Alvin Stewart
(74) *Attorney, Agent, or Firm* — Oliff PLC

(57) ABSTRACT

A joint part (1) has a porous portion (2) that is defined by a multiplicity of solid regions where material is present and a remaining multiplicity of pore regions where material is absent, the locations of at least most of the multiplicity of solid regions being defined by one or more mathematical functions. The nature of the porous portion can be varied systematically by changing one or more constants in the mathematical functions and the part is made by a process of solid freeform fabrication.

31 Claims, 8 Drawing Sheets

Figure 1:
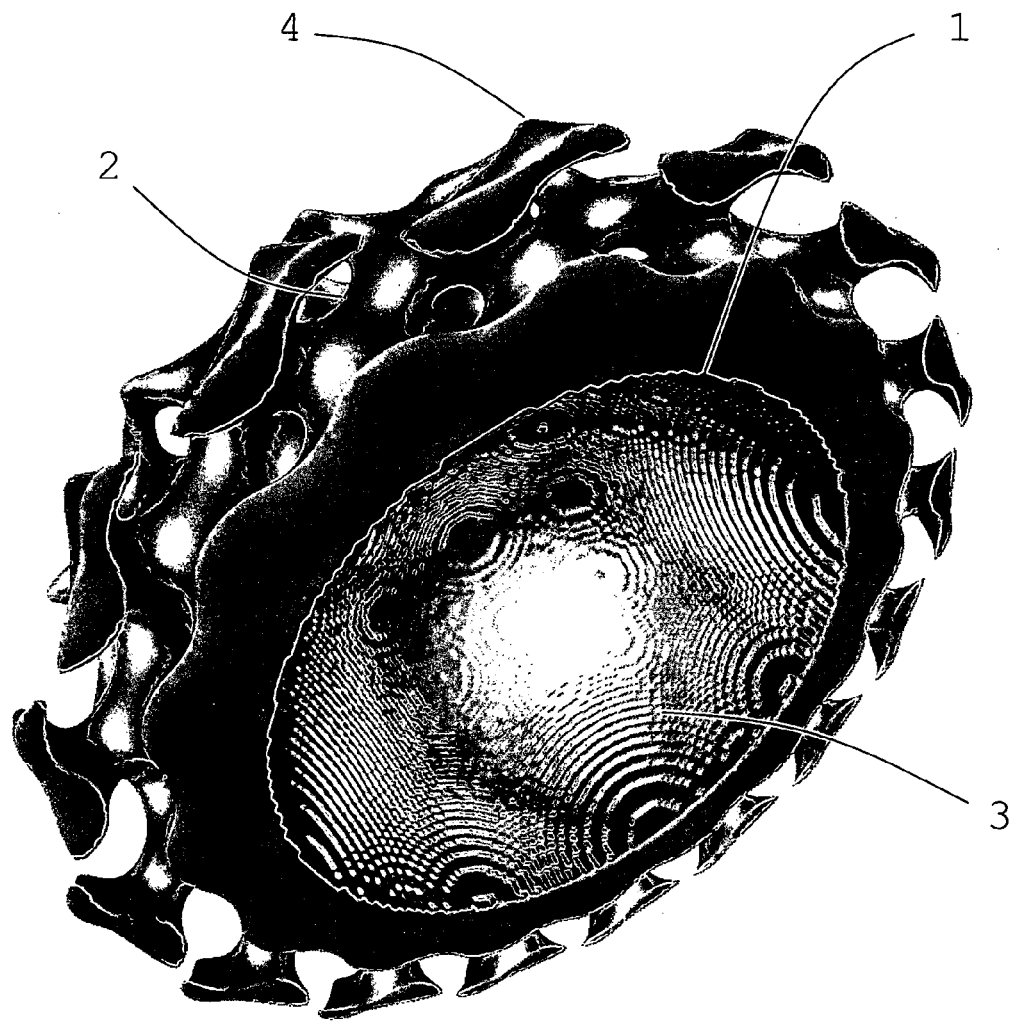

(51) Int. Cl.
*B22F 7/00* (2006.01)
*A61F 2/32* (2006.01)
*A61F 2/36* (2006.01)

(52) U.S. Cl.
CPC ........... *A61F2310/00023* (2013.01); *A61F 2310/00029* (2013.01); *A61F 2310/00179* (2013.01); *A61F 2310/00203* (2013.01); *A61F 2310/00239* (2013.01); *A61F 2310/00293* (2013.01); *A61F 2310/00329* (2013.01); *Y10T 29/4978* (2015.01)

(56) References Cited

U.S. PATENT DOCUMENTS

| | | | |
|---|---|---|---|
| 4,566,138 A * | 1/1986 | Lewis et al. | 623/22.38 |
| 4,608,052 A * | 8/1986 | Van Kampen et al. | 623/23.29 |
| 4,662,891 A * | 5/1987 | Noiles | 623/22.31 |
| 4,666,450 A * | 5/1987 | Kenna | 623/22.28 |
| 4,681,589 A * | 7/1987 | Tronzo | 623/22.32 |
| 4,778,474 A * | 10/1988 | Homsy | 623/22.14 |
| 4,813,959 A * | 3/1989 | Cremascoli | 623/22.27 |
| 4,828,565 A * | 5/1989 | Duthoit et al. | 623/22.3 |
| 4,828,566 A * | 5/1989 | Griss | 623/23.28 |
| 4,842,517 A * | 6/1989 | Kawahara et al. | 433/173 |
| 4,883,491 A * | 11/1989 | Mallory et al. | 623/22.31 |
| 4,904,265 A * | 2/1990 | MacCollum et al. | 623/22.28 |
| 4,955,909 A * | 9/1990 | Ersek et al. | 623/23.74 |
| 4,959,072 A * | 9/1990 | Morscher et al. | 623/22.33 |
| 5,011,494 A * | 4/1991 | von Recum et al. | 623/23.74 |
| 5,192,329 A * | 3/1993 | Christie et al. | 623/22.22 |
| 5,226,917 A * | 7/1993 | Schryver | 623/22.37 |
| 5,248,079 A * | 9/1993 | Li | 228/121 |
| 5,310,408 A * | 5/1994 | Schryver et al. | 623/22.37 |
| 5,348,788 A * | 9/1994 | White | 428/131 |
| 5,354,414 A * | 10/1994 | Feygin | 216/34 |
| 5,370,692 A * | 12/1994 | Fink et al. | 128/898 |
| 5,370,704 A * | 12/1994 | DeCarlo, Jr. | 623/22.22 |
| 5,455,100 A * | 10/1995 | White | 428/131 |
| 5,507,824 A * | 4/1996 | Lennox | 623/22.25 |
| 5,510,066 A * | 4/1996 | Fink et al. | 264/40.1 |
| 5,524,695 A * | 6/1996 | Schwartz | 164/34 |
| 5,549,691 A * | 8/1996 | Harwin | 623/22.37 |
| 5,571,185 A * | 11/1996 | Schug | 623/22.11 |
| 5,658,334 A * | 8/1997 | Caldarise et al. | 128/898 |
| 5,658,338 A * | 8/1997 | Tullos et al. | 623/22.39 |
| 5,716,414 A * | 2/1998 | Caldarise | 623/16.11 |
| 5,725,586 A * | 3/1998 | Sommerich | 623/23.35 |
| 5,779,833 A * | 7/1998 | Cawley et al. | 156/89.11 |
| 5,869,170 A * | 2/1999 | Cima et al. | 428/304.4 |
| 5,876,452 A * | 3/1999 | Athanasiou et al. | 623/23.72 |
| 5,879,398 A * | 3/1999 | Swarts et al. | 623/22.21 |
| 5,888,205 A * | 3/1999 | Pratt et al. | 623/22.35 |
| 5,897,592 A * | 4/1999 | Caldarise et al. | 128/898 |
| 6,013,853 A * | 1/2000 | Athanasiou et al. | 424/423 |
| 6,051,117 A * | 4/2000 | Novak et al. | 204/252 |
| 6,087,553 A * | 7/2000 | Cohen et al. | 623/22.21 |
| 6,187,329 B1 * | 2/2001 | Agrawal et al. | 424/426 |
| 6,206,924 B1 * | 3/2001 | Timm | 623/17.16 |
| 6,280,771 B1 * | 8/2001 | Monkhouse et al. | 424/484 |
| 6,283,997 B1 * | 9/2001 | Garg et al. | 623/16.11 |
| 6,290,726 B1 * | 9/2001 | Pope et al. | 623/22.15 |
| 6,293,971 B1 * | 9/2001 | Nelson et al. | 623/23.63 |
| 6,312,473 B1 * | 11/2001 | Oshida | 623/23.55 |
| 6,319,285 B1 * | 11/2001 | Chamier et al. | 623/22.32 |
| 6,451,059 B1 * | 9/2002 | Janas et al. | 623/23.51 |
| 6,454,811 B1 * | 9/2002 | Sherwood et al. | 623/23.76 |
| 6,488,715 B1 * | 12/2002 | Pope et al. | 623/22.21 |
| 6,494,918 B1 * | 12/2002 | Pope et al. | 623/23.6 |
| 6,514,518 B2 * | 2/2003 | Monkhouse et al. | 424/427 |
| 6,530,956 B1 * | 3/2003 | Mansmann | 623/18.11 |
| 6,547,994 B1 * | 4/2003 | Monkhouse et al. | 264/40.1 |
| 6,596,225 B1 * | 7/2003 | Pope et al. | 419/11 |
| 6,676,704 B1 * | 1/2004 | Pope et al. | 623/18.11 |
| 6,682,566 B2 * | 1/2004 | Draenert | 623/22.24 |
| 6,682,567 B1 * | 1/2004 | Schroeder | 623/22.24 |
| 6,709,462 B2 * | 3/2004 | Hanssen | 623/22.35 |
| 6,737,149 B1 * | 5/2004 | Wintermantel et al. | 428/131 |
| 6,840,960 B2 * | 1/2005 | Bubb | 623/23.5 |
| 6,858,042 B2 * | 2/2005 | Nadler et al. | 623/11.11 |
| 6,993,406 B1 * | 1/2006 | Cesarano et al. | 700/119 |
| 7,001,672 B2 * | 2/2006 | Justin et al. | 428/615 |
| 7,077,867 B1 * | 7/2006 | Pope et al. | 623/20.14 |
| 7,087,200 B2 * | 8/2006 | Taboas et al. | 264/49 |
| 7,122,057 B2 * | 10/2006 | Beam et al. | 623/23.51 |
| 7,235,107 B2 * | 6/2007 | Evans et al. | 623/23.51 |
| 7,300,668 B2 * | 11/2007 | Pryce Lewis et al. | 424/472 |
| 7,368,065 B2 * | 5/2008 | Yang et al. | 216/83 |
| 7,396,501 B2 * | 7/2008 | Pope et al. | 264/642 |
| 7,458,991 B2 * | 12/2008 | Wang et al. | 623/23.55 |
| 7,537,664 B2 * | 5/2009 | O'Neill et al. | 148/525 |
| 7,578,851 B2 * | 8/2009 | Dong et al. | 623/22.21 |
| 7,597,715 B2 * | 10/2009 | Brown et al. | 623/22.32 |
| 7,618,451 B2 * | 11/2009 | Berez et al. | 623/14.12 |
| 7,648,735 B2 * | 1/2010 | Hunter et al. | 427/248.1 |
| 7,674,426 B2 * | 3/2010 | Grohowski, Jr. | 419/2 |
| 7,674,477 B1 * | 3/2010 | Schmid et al. | 424/422 |
| 7,682,540 B2 * | 3/2010 | Boyan et al. | 264/212 |
| 7,695,521 B2 * | 4/2010 | Ely et al. | 623/22.21 |
| 7,718,109 B2 * | 5/2010 | Robb et al. | 264/308 |
| 7,718,351 B2 * | 5/2010 | Ying et al. | 430/322 |
| 7,740,795 B2 * | 6/2010 | Wang et al. | 419/2 |
| 7,758,643 B2 * | 7/2010 | Stone et al. | 623/14.12 |
| 7,771,485 B2 * | 8/2010 | Grundei | 623/23.11 |
| 7,815,826 B2 * | 10/2010 | Serdy et al. | 264/49 |
| 7,857,860 B2 * | 12/2010 | Saini et al. | 623/23.56 |
| 7,909,883 B2 * | 3/2011 | Sidebotham | 623/23.55 |
| 7,918,895 B2 * | 4/2011 | Isch et al. | 623/22.12 |
| 8,016,889 B2 * | 9/2011 | Dixon et al. | 623/17.14 |
| 8,080,483 B2 * | 12/2011 | Hillhouse et al. | 438/780 |
| 8,123,814 B2 * | 2/2012 | Meridew et al. | 623/22.28 |
| 8,133,284 B2 * | 3/2012 | Ely et al. | 623/22.11 |
| 8,163,566 B2 * | 4/2012 | Smith et al. | 436/518 |
| 8,197,550 B2 * | 6/2012 | Brown et al. | 623/22.32 |
| 8,268,383 B2 * | 9/2012 | Langhorn | 427/2.26 |
| 8,287,915 B2 * | 10/2012 | Clineff et al. | 424/602 |
| 8,308,810 B2 * | 11/2012 | Meridew | 623/22.19 |
| 8,556,972 B2 * | 10/2013 | Gordon et al. | 623/16.11 |
| 8,556,981 B2 * | 10/2013 | Jones et al. | 623/20.17 |
| 8,691,259 B2 * | 4/2014 | Bowman et al. | 424/422 |
| 8,702,808 B2 * | 4/2014 | Teoh et al. | 623/23.61 |
| 8,864,826 B2 * | 10/2014 | Pressacco | 623/11.11 |
| 2001/0039455 A1 * | 11/2001 | Simon et al. | 623/23.51 |
| 2002/0040245 A1 * | 4/2002 | Lester et al. | 623/22.23 |
| 2002/0062154 A1 * | 5/2002 | Ayers | 623/23.76 |
| 2002/0147499 A1 * | 10/2002 | Shea et al. | 623/22.21 |
| 2002/0182241 A1 * | 12/2002 | Borenstein et al. | 424/422 |
| 2002/0192263 A1 * | 12/2002 | Merboth et al. | 424/426 |
| 2003/0050705 A1 * | 3/2003 | Cueille et al. | 623/22.24 |
| 2003/0065400 A1 * | 4/2003 | Beam et al. | 623/23.51 |
| 2003/0105529 A1 * | 6/2003 | Synder et al. | 623/22.24 |
| 2003/0114936 A1 * | 6/2003 | Sherwood et al. | 623/23.58 |
| 2003/0135281 A1 * | 7/2003 | Hanssen | 623/22.35 |
| 2003/0153981 A1 * | 8/2003 | Wang et al. | 623/22.21 |
| 2004/0191106 A1 * | 9/2004 | O'Neill et al. | 419/2 |
| 2004/0204760 A1 * | 10/2004 | Fitz et al. | 623/14.12 |
| 2004/0210316 A1 * | 10/2004 | King et al. | 623/18.11 |
| 2004/0243237 A1 * | 12/2004 | Unwin et al. | 623/17.11 |
| 2005/0015088 A1 * | 1/2005 | Ringeisen | 606/69 |
| 2005/0027366 A1 * | 2/2005 | Saini et al. | 623/23.5 |
| 2005/0049706 A1 * | 3/2005 | Brodke et al. | 623/17.11 |
| 2005/0049715 A1 * | 3/2005 | Ito et al. | 623/23.5 |
| 2005/0102036 A1 * | 5/2005 | Bartee et al. | 623/23.76 |
| 2005/0112397 A1 * | 5/2005 | Rolfe et al. | 428/593 |
| 2005/0169893 A1 * | 8/2005 | Koblish et al. | 424/93.7 |
| 2005/0187638 A1 * | 8/2005 | Glien et al. | 623/23.56 |
| 2005/0251268 A1 * | 11/2005 | Truncale | 623/23.63 |
| 2005/0273176 A1 * | 12/2005 | Ely et al. | 623/23.32 |
| 2006/0116774 A1 * | 6/2006 | Jones et al. | 623/22.32 |
| 2006/0136071 A1 * | 6/2006 | Maspero et al. | 623/23.76 |
| 2006/0147332 A1 | 7/2006 | Jones et al. | |
| 2006/0178748 A1 * | 8/2006 | Dinger et al. | 623/18.11 |
| 2006/0178751 A1 * | 8/2006 | Despres et al. | 623/23.5 |
| 2006/0229715 A1 * | 10/2006 | Istephanous et al. | 623/1.46 |

(56) References Cited

U.S. PATENT DOCUMENTS

| | | | |
|---|---|---|---|
| 2006/0235542 A1* | 10/2006 | Hodorek et al. | 623/23.51 |
| 2006/0249875 A1* | 11/2006 | Robb et al. | 264/239 |
| 2006/0276925 A1* | 12/2006 | Lin et al. | 700/118 |
| 2006/0293760 A1* | 12/2006 | DeDeyne | 623/23.76 |
| 2007/0113951 A1* | 5/2007 | Huang | 156/89.11 |
| 2007/0116734 A1* | 5/2007 | Akash | 424/423 |
| 2007/0150068 A1* | 6/2007 | Dong et al. | 623/22.32 |
| 2007/0173948 A1* | 7/2007 | Meridew et al. | 623/22.24 |
| 2007/0191962 A1* | 8/2007 | Jones et al. | 623/22.32 |
| 2007/0203584 A1 | 8/2007 | Bandyopadhyay et al. | |
| 2007/0208428 A1* | 9/2007 | Tepic et al. | 623/22.32 |
| 2007/0233135 A1* | 10/2007 | Gil et al. | 606/86 |
| 2007/0233264 A1* | 10/2007 | Nycz et al. | 623/18.11 |
| 2007/0255412 A1* | 11/2007 | Hajaj et al. | 623/17.11 |
| 2007/0276506 A1* | 11/2007 | Troxel | 623/23.63 |
| 2008/0114465 A1* | 5/2008 | Zanella et al. | 623/23.6 |
| 2008/0195220 A1* | 8/2008 | Pope et al. | 623/22.17 |
| 2008/0288083 A1* | 11/2008 | Axelsson et al. | 623/23.51 |
| 2009/0017096 A1* | 1/2009 | Lowman et al. | 424/426 |
| 2009/0024229 A1* | 1/2009 | Chen et al. | 623/23.73 |
| 2009/0043398 A1* | 2/2009 | Yakimicki et al. | 623/23.51 |
| 2009/0112315 A1* | 4/2009 | Fang et al. | 623/11.11 |
| 2009/0162235 A1* | 6/2009 | Kita et al. | 419/2 |
| 2009/0192610 A1* | 7/2009 | Case et al. | 623/16.11 |
| 2009/0326674 A1* | 12/2009 | Liu et al. | 623/23.55 |
| 2010/0047309 A1* | 2/2010 | Lu et al. | 424/423 |
| 2010/0075419 A1* | 3/2010 | Inagaki et al. | 435/402 |
| 2010/0100123 A1* | 4/2010 | Bennett | 606/213 |
| 2010/0131074 A1* | 5/2010 | Shikinami | 623/23.5 |
| 2010/0137990 A1* | 6/2010 | Apatsidis et al. | 623/17.16 |
| 2010/0198353 A1* | 8/2010 | Pope et al. | 623/17.11 |
| 2010/0222892 A1* | 9/2010 | Linares | 623/23.5 |
| 2010/0291178 A1* | 11/2010 | Lu et al. | 424/423 |
| 2010/0292791 A1* | 11/2010 | Lu et al. | 623/13.12 |
| 2011/0014081 A1* | 1/2011 | Jones et al. | 419/2 |
| 2011/0015752 A1* | 1/2011 | Meridew | 623/22.24 |
| 2011/0022180 A1* | 1/2011 | Melkent et al. | 623/23.5 |
| 2011/0022181 A1* | 1/2011 | Kasahara et al. | 623/23.5 |
| 2011/0064784 A1* | 3/2011 | Mullens et al. | 424/443 |
| 2011/0125284 A1* | 5/2011 | Gabbrielli et al. | 623/23.4 |
| 2011/0172798 A1* | 7/2011 | Staiger et al. | 700/98 |
| 2011/0240997 A1* | 10/2011 | Rockenberger et al. | 257/49 |
| 2011/0278533 A1* | 11/2011 | Hillhouse et al. | 257/9 |
| 2011/0287167 A1* | 11/2011 | Wei et al. | 427/2.1 |
| 2012/0022662 A1* | 1/2012 | Conway et al. | 623/22.21 |
| 2012/0209396 A1* | 8/2012 | Myung et al. | 623/22.11 |
| 2012/0271361 A1* | 10/2012 | Zhou et al. | 606/304 |
| 2013/0006354 A1* | 1/2013 | Pressacco | 623/11.11 |
| 2013/0174287 A1* | 7/2013 | Higuera et al. | 800/8 |
| 2013/0178947 A1* | 7/2013 | Monaghan et al. | 623/23.55 |
| 2013/0190889 A1* | 7/2013 | Li et al. | 623/23.11 |

OTHER PUBLICATIONS

Dec. 11, 2015 Office Action issued in European Application No. 08 788 557.0.

STL (file format), Wikipedia (Nov. 27, 2007), https://web.archive.org/web/20071127234105/http://en.wikipedia.org/wiki/STL_(file_format).

Rapid Prototyping, Wikipedia (Feb. 16, 2008), https://web.archive.org/web/20080216183011/http://en.wikipedia.org/wiki/Rapid_Prototyping.

Selective Laser Sintering, Wikipedia (Feb. 25, 2008), https://web.archive.org/web/20080225182722/http://en.wikipedia.org/wiki/Selective_laser_sintering.

Gean Vitor Salmoria et al., Rapid Manufacturing of Polyethylene Parts with Controlled Pore Size Gradients Using Selective Laser Sintering, 10 Materials Research 211 (2007).

* cited by examiner

RELATING TO JOINTS AND/OR IMPLANTS

CROSS REFERENCE TO RELATED APPLICATIONS

This application is the United States national phase filing of the corresponding international application number PCT/GB2008/003027, filed on Sep. 8, 2008, which claims priority to and benefit of GB Application No. 0809721.4, filed May 28, 2008, which applications are hereby incorporated by reference in their entirety.

This invention relates to joints and joint parts for medical and non-medical use and to implants suitable for implanting in a human body in place of bone, and also to methods of making such joints or implants. The invention is more particularly, but not exclusively, directed to joint parts, for example, ball and socket joints, for use in all kinds of applications, including non-medical applications and to load-bearing implants that are able to be implanted without the use of cement and provide a major part of, or the whole of, one part of a joint, for example a component of a hip, knee, ankle, shoulder, elbow or wrist.

The particular requirements of an implant suitable for implanting in a human body vary very much according to the application. Broadly there are two kinds of bone implant. Firstly, there are those that are used in tissue engineering applications to provide a scaffold in which bone tissue may be encouraged to grow; implants of this kind, which may be used for small reconstruction and repair applications, do not themselves have great structural strength and are often in the form of thin sheets or blocks. Secondly, there are those that are used to replace all or part of a joint, or in other load bearing applications. Such implants are often of a particular curved shape and may be required to bear substantial loads; in that respect, their strength is important, but it is also important that they can be fixed securely in position; such fixing can be carried out by using a suitable cement but it is preferred where possible to provide an implant which can be integrated into existing bone material through natural incursion of biological tissue into one or more portions of the implant. Considerations of the kind just described may lead to implants of composite construction, with a first part having the necessary strength and other properties to enable it to act as part of a joint and a second part formed separately from the first part and being able to be integrated into, and thus fixed securely to, adjacent or surrounding bone material.

Key properties of a load bearing implant are its mechanical strength and its porosity. A common approach when creating an implant is to adopt a trial and error approach to finding an implant with desired porosity and strength characteristics. Thus a first prototype implant may be made and its physical properties tested. Thereafter a modified version of the prototype may be manufactured with an altered structure to effect a change to the porosity and/or strength of the implant. A difficulty that is often encountered in this process is seeking to assess quantitatively the effect on porosity and strength of a given change in the structure. That applies when the structure is of uniform strength and porosity throughout, but it is all the more problematic where it is desired to provide variation in the porosity and/or strength of the implant from one region of the structure to another.

In a paper entitled "Fabrication methods of porous metals for use in orthopaedic applications" by Ryan, Pandit and Apatsidis published in Biomaterials 27 (2006) 2651-2670, a range of methods of making metal implants are reviewed. Those methods include one using rapid prototyping technology to create porous shapes from a multiplicity of cubic elements. Whilst using such rapid prototyping technology as taught in the paper can speed up the production of an implant, it does not make it any easier to adjust the characteristics of the implant in a predictable and systematic manner, for example to effect a preselected increase in the porosity of the implant.

Rapid prototyping techniques are used in a wide variety of applications including many non-medical applications and the disadvantage of not being able easily to predict the characteristics of a product made by such techniques is disadvantageous in those applications too.

It is an object of the invention to provide an improved joint part and an improved method of making a joint part.

It is a further object of the invention to provide an improved implant and to provide an improved method of making an implant.

According to the invention there is provided a joint part having a porous portion that is defined by a multiplicity of solid regions where material is present and a remaining multiplicity of pore regions where material is absent, the locations of at least most of the multiplicity of solid regions being defined by one or more mathematical functions. The invention further provides a joint including a joint part as defined immediately above.

According to the invention there is also provided a load-bearing implant having a porous portion that is defined by a multiplicity of solid regions where material is present and a remaining multiplicity of pore regions where material is absent, the locations of at least most of the multiplicity of regions where material is present being defined by one or more mathematical functions.

According to the invention there is further provided a method of making a load-bearing implant having a porous portion defined by a multiplicity of solid regions where material is present and a remaining multiplicity of pore regions where material is absent, the method including the step of depositing solid material in the multiplicity of solid regions during a process of solid freeform fabrication in which one or more mathematical functions are used to determine at least most of the multiplicity of regions where material is present.

By defining the solid regions mathematically, it becomes much simpler to vary the nature of the porous portion in a systematic way that will have predictable results in terms of its effect on mechanical strength and porosity. It is only necessary to change the values of one or more constants in the mathematical functions defining the solid regions and an implant with different and varying characteristics of porosity and strength can readily be produced. Where reference is made to determining regions where material is present, it should be understood that this may involve determining all the regions where material is absent (the negative image) or it may involve (as in a preferred embodiment of the invention described below) determining the boundary surface of the solid regions.

Preferably, the method of the invention further includes the step of modifying one or more of the mathematical functions to vary the porosity and/or strength of the porous portion, calculating the porosity and/or strength of the modified porous portion and making the joint part or implant with the modified porous portion, the method including the step of depositing solid material during a process of solid freeform fabrication in which the one or more modified mathematical functions are used to determine at least most of the multiplicity of regions where material is present.

It is within the scope of the invention for some portion(s) of the joint part or implant to be defined in a non-mathematical way, but in a preferred embodiment of the invention all the solid regions of the joint part or implant are defined mathematically.

Where reference is made herein to solid freeform fabrication, it should be understood that there are many known methods of this kind and that the invention is not limited to any particular kind of such fabrication, nor indeed is it concerned with which method is adopted. Any appropriate method may be employed. Typically, in a solid freeform fabrication (SSF), material is laid down in a multiplicity of thin layers each layer being laid in a respective pattern and fixed to the layer below. In that way a three dimensional shape of any desired kind, including re-entrant surfaces and the like can be formed. Machines which provide for solid freeform fabrication are sometimes referred to as rapid prototyping machines, but it should be understood that in the present invention the products produced may not only be prototypes but also final products.

Preferably the one or more mathematical functions define a periodic nodal surface as a boundary surface between solid and pore regions. Suitable periodic nodal surfaces are triply periodic surfaces, namely the primitive (P) surface, the diamond (D) surface and the gyroid (G) surface. Mathematically, those surfaces arise from defining a surface S between the solid and pore regions $$S: F(X)=0, X \in R^3$$

where X is a point of coordinates x, y and z. A porosity gradient may be introduced into a structure by adding a linear term to the above equation. Alternatively or additionally, a radial porosity gradient may be introduced using a radial term in a cylindrical geometry. A trigonometric polynomial may be used for the definition of the function F(X), which can be written as a sum of d terms:

$$1 + \sum_{c=1}^{d} a_c \sin^i x \cdot \sin^j y \cdot \sin^k z \cdot \cos^l x \cdot \cos^m y \cdot \cos^n z \quad i, j, k, l, m, n = 0, 1.$$

That gives rise to the above-mentioned primitive, diamond and gyroid surfaces having interconnectivity orders equal to 6, 4 and 3 respectively. From a topological point of view, the interconnectivity order refers to how many struts depart from each node of the lattice. A primitive surface may also be referred to as a cubic surface and a diamond surface may also be referred to as a tetrahedral surface. In an example of the invention defined below, a set of inequalities for defining a gyroidal (G) structure is given as one example of an appropriate mathematical function.

Optionally, roughness can be introduced into the above equations as a term with a higher angular frequency. Thus the curvature may be changed locally. For example, introducing such roughness in biological applications may improve cell adhesion and growth.

The joint part or implant may be made of a metal material and this may most commonly be the case, but the invention may be employed with any of a wide variety of materials. For example, it has recently become feasible to deposit ceramic materials using a solid freeform fabrication technique and the implant of the invention may thus be formed of ceramic material. As well it is possible to deposit polymeric materials using a solid freeform fabrication technique and the implant of the invention may thus be formed also of polymeric material. Examples of metal materials that may be employed include: stainless steel; titanium alloys; and cobalt chrome alloys. Examples of ceramic materials that may be employed include: calcium phosphate based materials such as ones including calcium phosphate, tricalcium phosphate (TCP), hydroxyapatite (HA), HA/TCP blends, HA/barium titanate blends, ion substituted HA and bioglass; zirconia; alumina; and zirconia toughened alumina. Examples of polymeric materials that may be employed are ultra high molecular weight polyethylene (UHMWPE); blends of UHMWPE with ceramic material; polyurethanes; silicones; polymethylmethacrylate (PMMA); and bioresorbable polymers.

The joint part or implant may consist exclusively of the porous portion or it May also include a solid portion. The latter is more usual. The "solid" portion may have some level of porosity, provided the level is substantially less than the porosity of the porous portion, but preferably the solid portion has no porosity. The porous portion preferably has a porosity, which may be no porosity, in the region bordering the solid region substantially equal to the porosity of the solid region and increases in porosity away from the solid portion. The increase in porosity is preferably gradual and more preferably without any discontinuity. It is a particular advantage of the present invention that it can become a straightforward matter to avoid discontinuities in physical properties of the porous portion and thereby enable regions of especially high stress to be avoided. Thus there may be a continuous change in porosity through a region of the joint part or implant.

The solid portion preferably has a curved bearing surface. For example, the solid portion may define a cup, which may provide part or all of the socket of a ball and socket joint; in this case the cup may have a concave load bearing, cup portion which is solid and may have a porous portion extending outwardly from the cup portion to a peripheral outer surface. Similarly, the solid portion may define a ball, which may provide part or all of the ball of a ball and socket joint; in this case the ball may have a convex load bearing ball portion which is solid and may have a porous portion extending away from the ball portion.

By way of example, for a femoral head, the ball head of the ball and socket joint needs to be as highly polished and smooth as possible to reduce friction and wear. However, the invention may for example be applied to the proximal (upper) portion, for example the upper third, of the femoral stem. Such an arrangement can promote bone ingrowth and enhanced fixation in the femur where it is desirable and needed.

For a joint part for use in other applications, especially non-medical applications, it may be acceptable or even desirable for a bearing surface of the joint part to be porous, for example to provide a path for lubricant to reach the bearing surfaces.

In the case where the joint part or implant includes a solid portion, the solid portion may be formed by the solid freeform fabrication technique, and the solid portion and the porous portion are preferably made in one piece. Thus, the method of the invention may be one in which the joint part or implant includes a solid portion and a porous portion, the solid portion and the porous portion being formed in the same process of solid freeform fabrication to provide a one-piece integrated structure.

The invention may, for example, be employed in an orthopaedic or dental application. In particular, the invention may be employed in an acetabular cup for a hip joint. Thus, in an especially preferred form the invention may provide an acetabular cup having an inner cup-shaped surface and a porous portion that extends outwardly to a peripheral outer porous surface, the porous portion being defined by a multiplicity of solid regions where material is present and a remaining multiplicity of pore regions where material is absent, at least most of the multiplicity of regions where material is present being defined by one or more mathematical functions. Similarly, the invention may provide a method of making an acetabular cup, having an inner cup-shaped surface and a porous portion that extends outwardly to a peripheral outer porous surface, the porous portion being defined by a multiplicity of solid regions where material is present and a remaining multiplicity of pore regions where material is absent, the method including the step of depositing solid material in the multiplicity of solid regions during a process of solid freeform fabrication in which one or more mathematical functions are used to determine at least most of the multiplicity of regions where material is present.

Whilst certain features of the invention have been described in relation to a bone implant or joint part and not described in relation to a method of making an implant or joint part, it should be understood that those features may be used in the method. Similarly features described only in relation to the method may also be applied to an implant according to the invention. Finally, features described in relation to a bone implant may be used in a joint part and vice versa.

Figure 2:
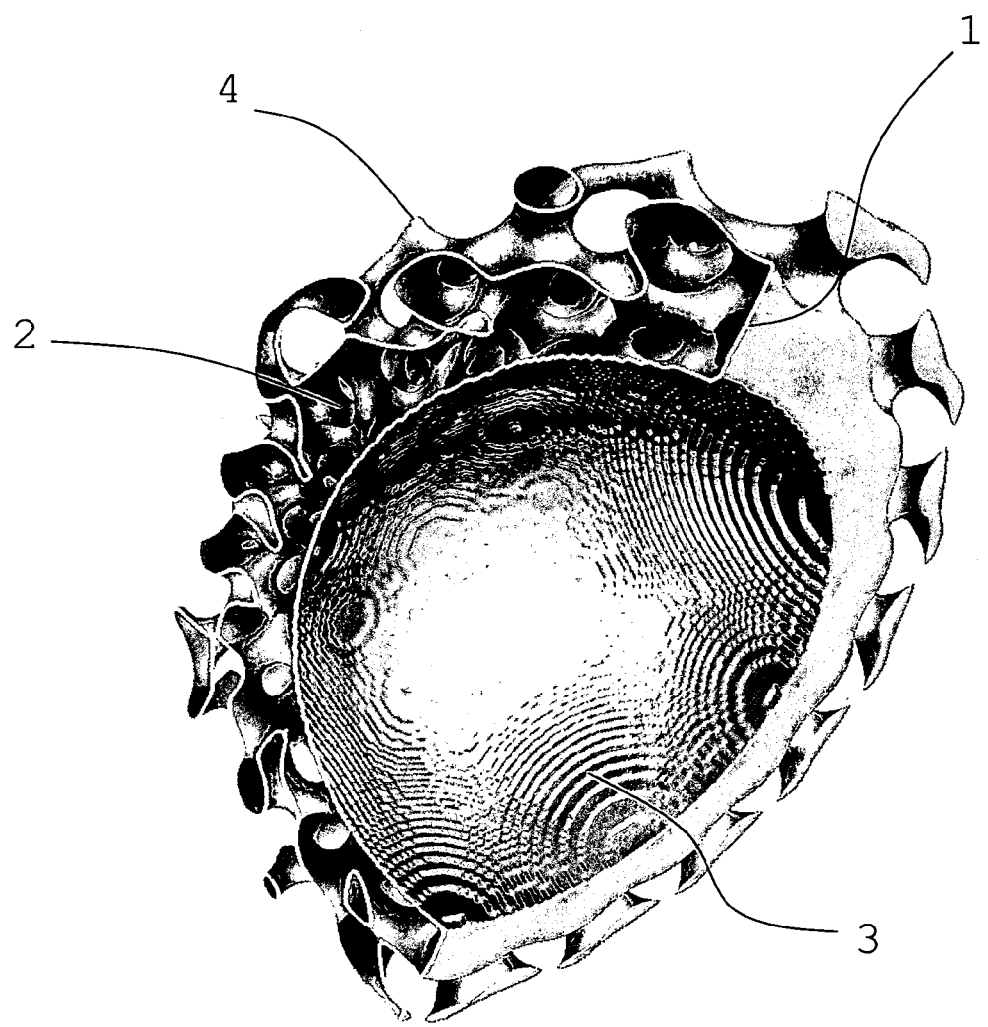
Figure 3:
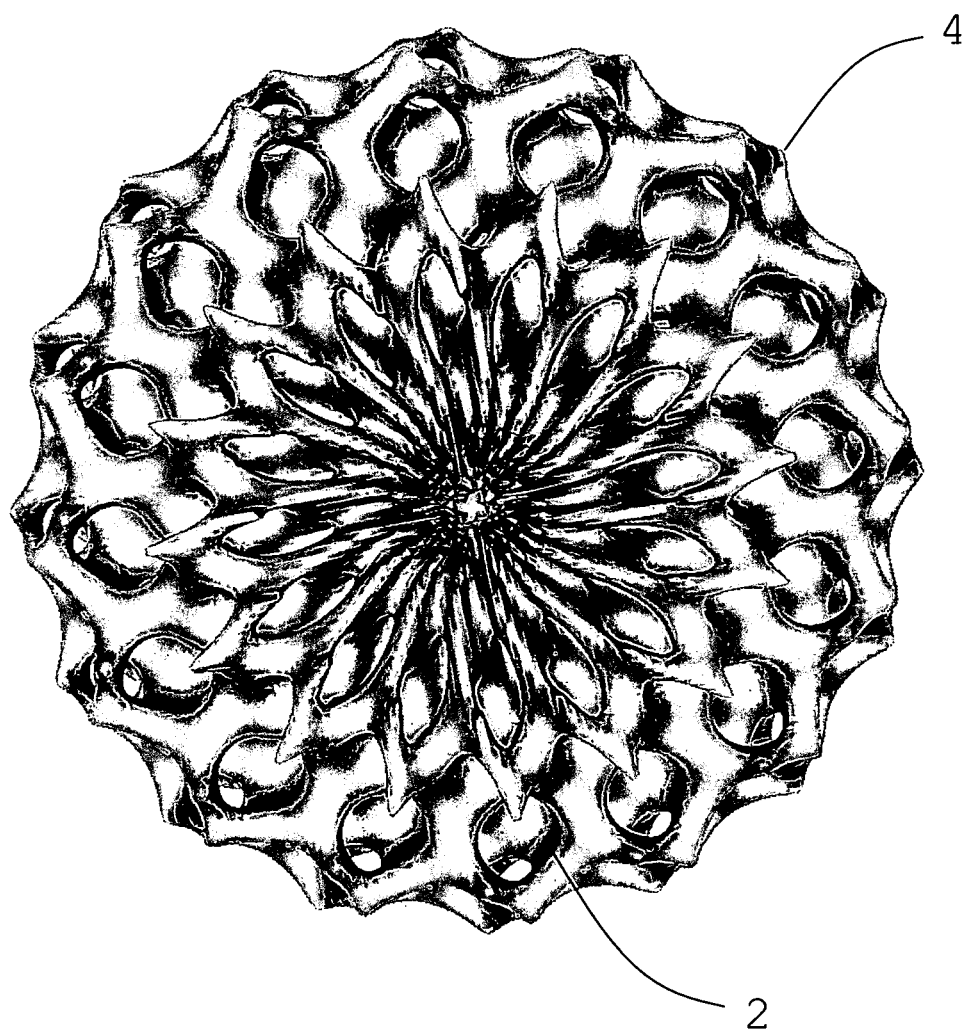
Figure 4:
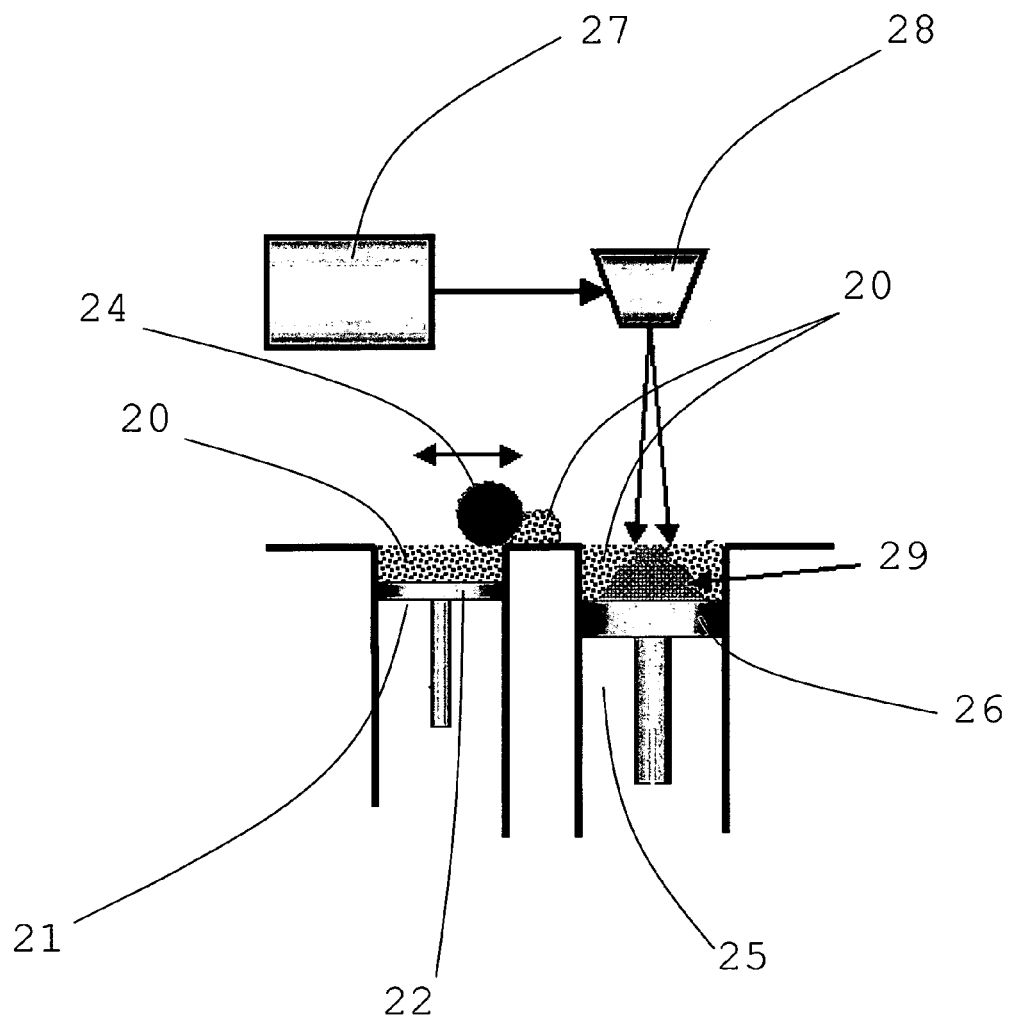
Figure 5:
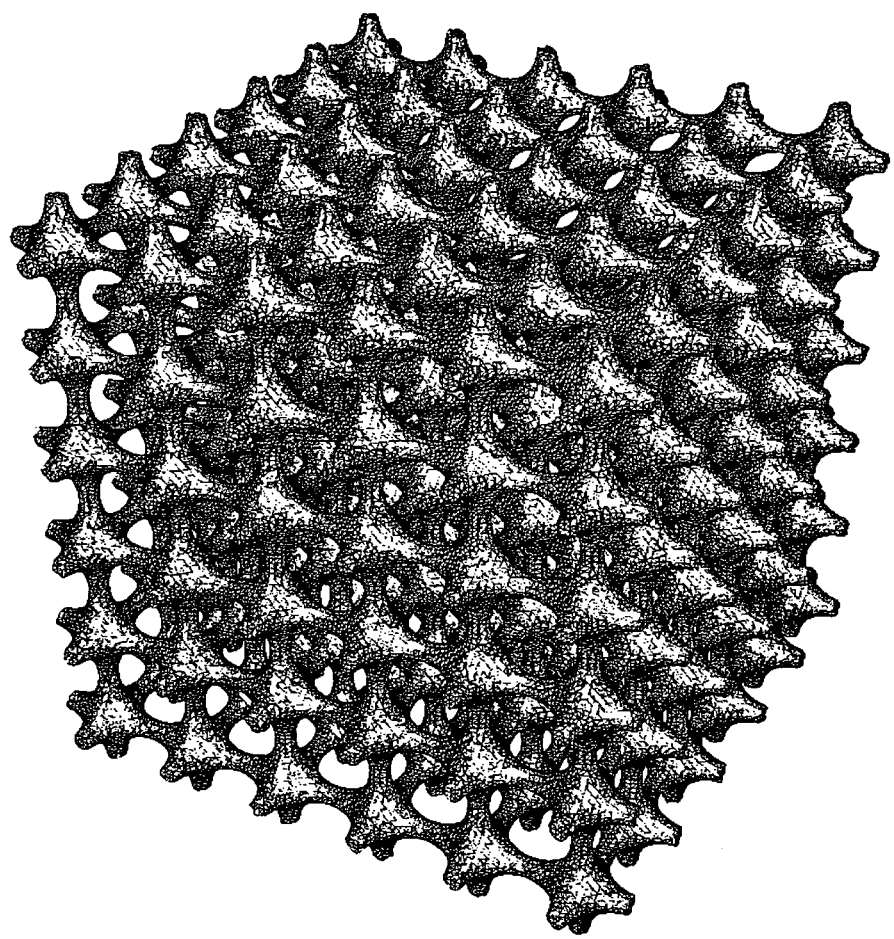
Figure 6:
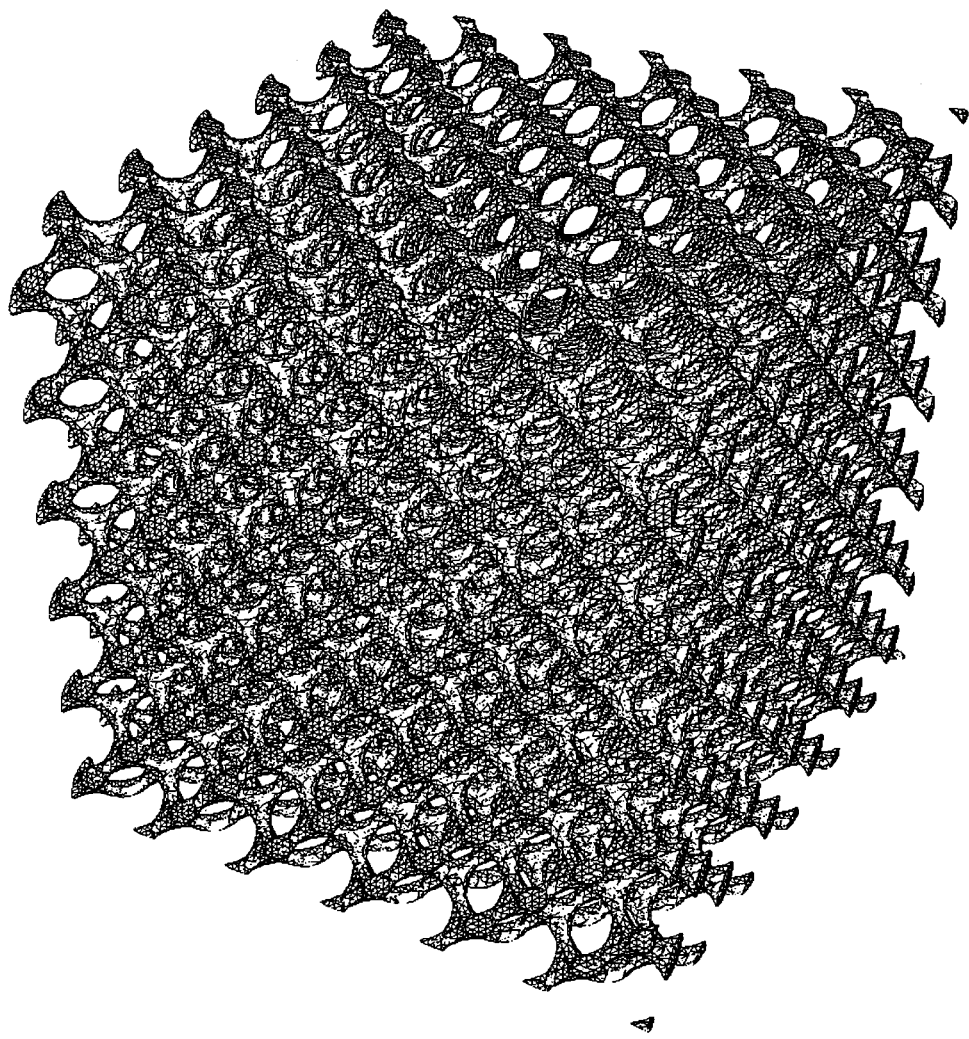
Figure 7:
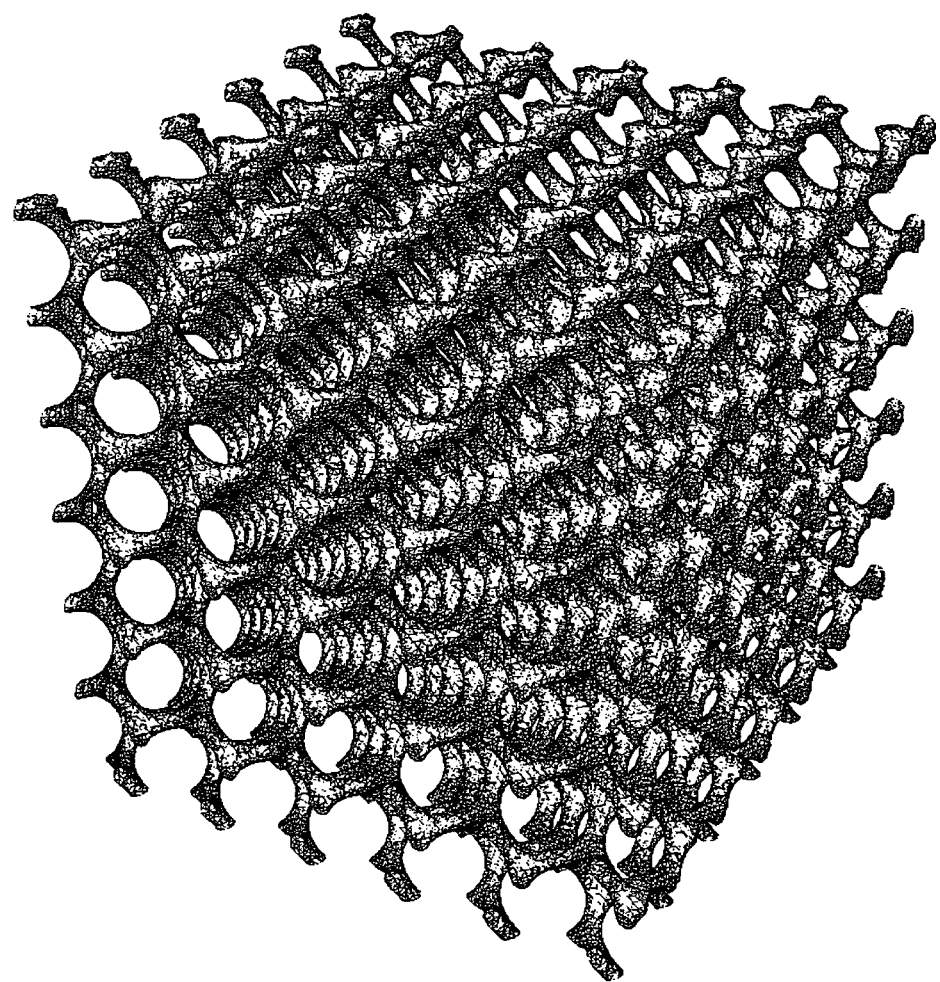
Figure 8:
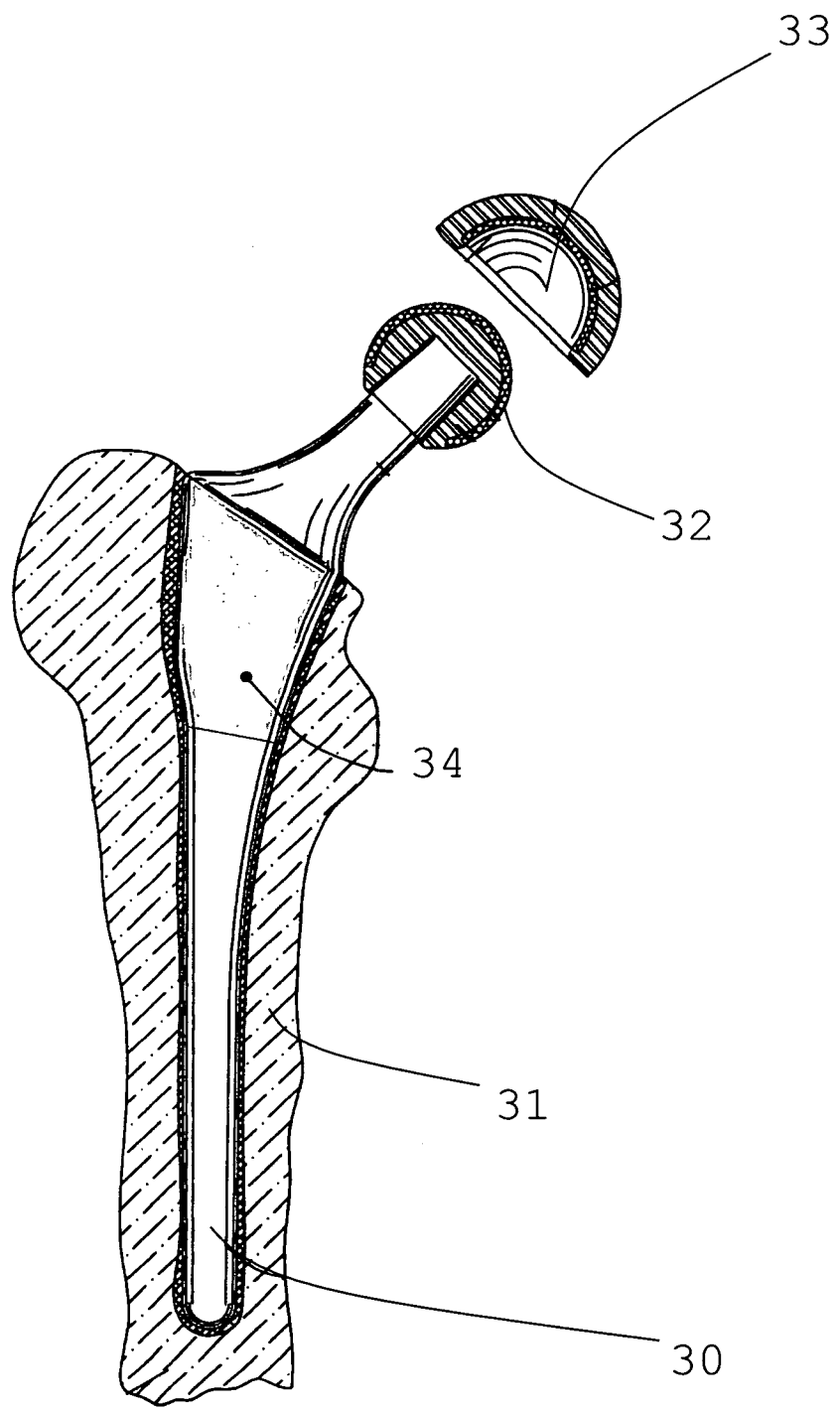

By way of example embodiments of the invention will now be described with reference to the accompanying drawings of which:

FIG. 1 is a view of a complete acetabular cup;
FIG. 2 is a sectional view of the acetabular cup;
FIG. 3 is an end view of the acetabular cup;
FIG. 4 is a schematic view of a rapid prototyping process suitable for forming the acetabular cup of FIG. 3;
FIG. 5 is an isometric view of a basic cubic shape generated from modelling a primitive (P) surface;
FIG. 6 is an isometric view of a basic cubic shape generated from modelling a diamond (D) surface;
FIG. 7 is an isometric view of a basic cubic shape generated from modelling a gyroid (G) surface; and
FIG. 8 is a partly exploded sectional view of a hip joint.

FIGS. 1 to 3 show, by way of example, the application of the invention to one particular implant, namely an acetabular cup. The complete cup is shown in FIG. 1 and generally comprises an inner cup-shaped portion 1 and an outer porous portion 2. The inner cup-shaped portion 1 has a generally hemispherical concave surface 3 which provides a bearing surface of the socket of a hip joint. The inner cup-shaped portion 1 is not porous and has a thickness chosen to impart sufficient strength and rigidity to the bearing surface 3. The porous portion 2 has a porosity which increases gradually from zero to a significant level toward an outer surface 4 of the cup. The sizes of the individual pores also increase toward the outer surface 4 of the cup.

Three dimensional modelling of a part such as the porous portion 2 is traditionally carried out by adding primitives such as spheres, cylinders, boxes and other shapes, by rotating two dimensional shapes to form solids of revolution, and by making use of Boolean operations such as union, intersection or subtraction on the solids created. Parts created in this manner will then have measurable values of porosity and strength, but it is not easy to predict how altering the part will alter its porosity and shape, nor is it easy to provide for a continuous smooth transition in the properties of the part from one region to another.

In accordance with the present invention, the three dimensional modelling of the acetabular cup is carried out using mathematical functions. The functions chosen can be relatively simple whilst still providing the desired properties. Of particular advantage for the modelling are the triply periodic surfaces that can be defined simply in mathematical functions using x, y and z coordinates. Three such surfaces are the primitive (P) surface, the diamond (D) surface and the gyroid (G) surface, having interconnectivity orders respectively equal to 6, 4 and 3 respectively. The primitive surface can be defined by the equation:

$$a_1(\cos x + \cos y + \cos z) + a_2(\cos x \cos y + \cos y \cos z + \cos z \cos x) + 1 = 0$$

Similarly, the diamond surface can be defined by the equation:

$$a_3(\sin x \sin y \sin z + \sin x \cos y \cos z + \cos x \sin y \cos z + \cos x \cos y \sin z) + a_4[\cos(4x) + \cos(4y) + \cos(4z)] + 1 = 0$$

And the gyroid (G) surface can be defined by the equation:

$$a_5(\cos x \sin y + \cos y \sin z + \cos z \sin y) + a_6[\cos(2x)\cos(2y) + \cos(2y)\cos(2z) + \cos(2z)\cos(2x)] + 1 = 0$$

Where the constants $a_1$ to $a_6$ are chosen according to the particular surface of given topology that is to be defined. For example, the constants $a_1$ to $a_6$ may be used to control the global porosity or the neck diameter to node radius ratio. The scale factor (i.e. the pore size) may also be controlled.

As will be appreciated, the porous portion defined by the Primitive surface has the topological characteristic of 6 struts per node, the diamond surface has the topological characteristic of 4 struts per node and the gyroid surface has the topological characteristic of 3 struts per node (the minimum). These surfaces can be used, in accordance with the invention, to define the boundary between the solid material and the pores. In that way a complex structure can be defined in relatively simple mathematical terms. It is then possible to modify the structure by adjustment of the constants $a_1$ to $a_6$, and to analyse the changes in porosity and strength that any such changes to the constants cause.

The approach set out immediately above is further explained below with reference to FIGS. 1 to 3. In those examples an acetabular cup defined by gyroid (G) surfaces is shown. More specifically the locations of the solid regions of the cup are defined by the following set of inequalities:

$$z > 0$$

$$x^2 + y^2 + z^2 > r_i^2$$

$$\cos r \sin n\theta + \cos n\theta \sin n\phi + \cos n\phi \sin r + ar - b < 0$$

where $$r = \sqrt{x^2 + y^2 + z^2}$$

$$\theta = \arctan \frac{y}{x} \qquad \phi = \arctan \frac{z}{\sqrt{x^2 + y^2 + z^2}}$$

with the parameters:
$r_i$ internal radius of the porous portion of the cup
n circumferential resolution (number of features)
a porosity gradient
b porosity offset Shapes that can be generated by these inequalities are shown in FIGS. 1 to 3. As can be seen the porosity of the porous portions and the sizes of the pores increase outwardly, facilitating the natural incursion of material into the implant when it is in use and thus providing secure fixing of the implant.

As will now be understood the porosity gradient can readily be changed simply by changing the value of a in the inequality above and the porosity offset, that is the thickness of the inner, non-porous part, can readily be changed simply by changing the value of b in the inequality above.

Because the locations of the solid regions are defined by simple mathematical functions it is straightforward to program a rapid prototyping machine to make the cup. For example machines using Laser or electron beam energy sources to melt the raw material in powder may be employed. As will be understood those machines can make the entire cup of FIG. 1, including both the solid inner portion and the porous outer portion, in a single process.

If it is then desired to produce a cup having different properties of porosity and strength one or more of the constants in the inequalities given above can be altered to produce a predictable variation in the properties. Since the structure shape is mathematically defined it is relatively easy to analyse its porosity and other properties.

FIG. 4 shows in schematic form one example of a rapid prototyping machine that may be used to make the shapes shown in FIGS. 1 to 3 and other shapes. In the example shown powder material 20 from which the shaped part is to be formed is stored in a cylindrical chamber 21. By raising a piston 22 in the chamber 21 by one step powder material can be transferred by a roller 24 into a cylindrical chamber 25. The bottom of the chamber 25 is defined by a piston 26 and each time the piston 22 is raised by one step, the piston 26 is lowered by one step and a new layer of powder material deposited in the top of the chamber 25. A laser 27 and scanner 28 apply a beam of narrowly focussed energy onto the top layer of powder in the chamber 25 in a two dimensional pattern determined by the machine. Powder material exposed to the beam is fused while the other material remains in powder form. The process is repeated many times with different two dimensional patterns for different layers so that a solid object 29 of a predetermined shape is formed in the chamber 25. Once the object is fully formed it is removed from the chamber and the powder material from the chamber 25 discarded or recycled.

As will be understood, FIG. 4 shows one form of rapid prototyping machine, simply by way of example. Many other forms of machine may also be used.

In FIGS. 1 to 3, the particular shape shown is one generated from modelling a gyroid (G) surface. Reference has also been made above to Primitive (P) surfaces and diamond (D) surfaces. By way of example, FIGS. 5 to 7 show basic cubic shapes generated from modelling a primitive (P) surface, a diamond (D) surface and a gyroid (G) surface.

In the example given above, simple mathematical functions have been described but it will be understood that it is within the scope of the invention to adopt more complex functions, for example to produce more complex shapes, if desired.

Whilst in FIGS. 1 to 3, the invention is shown applied to an acetabular cup, it should be understood that the invention may also be applied to other parts of a hip joint (and indeed other joints). By way of example, FIG. 8 shows a hip joint in which a femoral stem 30 is implanted in the top of a femur 31 and carries a coated ball joint 32 on the top of the stem. The joint 32 is received in a coated acetabular cup 33. An upper portion 34 of the femoral stem 30 may be formed of porous material and may advantageously be of varying porosity. By making the femoral stem in accordance with the invention the porosity gradient in the portion 34 of the stem 30 can readily be controlled.

One particular way in which the invention may be employed involves the following steps:

1. Making a joint part having a porous portion using a process of solid freeform fabrication in a machine where a mathematical function is used to determine the programming of the machine.
2. Assessing certain physical properties of the porous portion, for example the porosity and/or the mechanical strength.
3. Repeating step 1 using the same mathematical function but with at least one constant in the mathematical function changed to produce a part having different physical properties.
4. Optionally, repeating step 3 with other values of constant.

By adopting a method of the kind outlined above it becomes relatively easy to make a range of parts of different, controlled, porosities and then to evaluate which particular porosity is most suited for a particular application.

The invention claimed is:

1. A joint part comprising a porous portion, the porous portion having:
   a multiplicity of solid regions where material is present, locations of at least most of the multiplicity of solid regions being defined by one or more mathematical functions; and
   a remaining multiplicity of pore regions where material is absent,
   wherein the one or more mathematical functions define the solid region locations so that the locations of the remaining multiplicity of pore regions are nonrandom, and
   wherein the one or more mathematical functions include at least one term that defines a porosity gradient such that porosity of at least part of the porous portion changes continuously and without any discontinuity.

2. A joint part according to claim 1, in which the locations of all the solid regions of the joint part are defined mathematically.

3. A joint part according to claim 1, in which the one or more mathematical functions define a periodic nodal surface as a boundary surface between the solid and the pore regions.

4. A joint part according to claim 3, in which the periodic nodal surface is selected from the group comprising a primitive (P) surface, a diamond (D) surface and a gyroid (G) surface, the primitive (P) surface, the diamond (D) surface, and the gyroid (G) surface having interconnectivity orders equal to 6, 4, and 3, respectively.

5. A joint part according to claim 4, in which the periodic nodal surface is selected from the group consisting of the primitive (P) surface, the diamond (D) surface, and the gyroid (G) surface.

6. A joint part according to claim 1, in which the joint part further includes a solid portion, the porous portion and the solid portion being part of the same single piece.

7. A joint part accordingly to claim 6, in which the porosity of the porous portion in the region bordering the solid portion is substantially equal to the porosity of the solid portion, the porosity of the porous portion increasing away from the solid portion.

8. A joint part according to claim 1, in which the joint part is a ball and socket joint.

9. A joint part according to claim 8, in which the porous portion defines a socket of the ball and socket joint.

10. A joint part according to claim 9, in which the socket has a concave load-bearing cup portion which is solid and the porous portion extends outwardly from the cup portion to a peripheral outer surface.

11. A joint part according to claim 8, in which the porous portion defines a ball of the ball and socket joint.

12. A joint part according to claim 11, in which the ball has a convex load-bearing ball portion which is solid and the porous portion extends away from the ball portion.

13. A joint part according to claim 1, in which the joint part is a load-bearing implant suitable for implanting in a human body.

14. A joint part according to claim 1, in which the one or more mathematical functions define the distance between adjacent solid regions of the multiplicity of solid regions.

15. A joint part according to claim 1, in which each of the solid regions in the multiplicity of solid regions has the same contour as the other solid regions.

16. A joint part according to claim 1, in which the at least one term comprises a linear term.

17. A joint part according to claim 1, in which the at least one term comprises a radial term.

18. A load-bearing implant comprising a porous portion, the porous portion having:
   a multiplicity of solid regions where material is present, locations of at least most of the multiplicity of solid regions being defined by one or more mathematical functions; and
   a remaining multiplicity of pore regions where material is absent,
   wherein the one or more mathematical functions define the solid region locations so that the locations of the remaining multiplicity of pore regions are nonrandom, and
   wherein the one or more mathematical functions include at least one term that defines a porosity gradient such that porosity of at least part of the porous portion changes continuously and without any discontinuity.

19. A load-bearing implant according to claim 18, in which the locations of all the solid regions of the implant are defined mathematically.

20. A load-bearing implant according to claim 18, in which the one or more mathematical functions define a periodic nodal surface as a boundary surface between the solid and the pore regions.

21. A load-bearing implant according to claim 20, in which the periodic nodal surface is selected from the group comprising a primitive (P) surface, a diamond (D) surface and a gyroid (G) surface, the primitive (P) surface, the diamond (D) surface, and the gyroid (G) surface having interconnectivity orders equal to 6, 4, and 3, respectively.

22. A load-bearing implant according to claim 18, in which the implant is made of metal.

23. A load-bearing implant according to claim 18, in which the implant is made of ceramic material.

24. A load-bearing implant according to claim 18, in which the implant is made of polymeric material.

25. A load-bearing implant according to claim 18, in which the implant further includes a solid portion, the porous portion and the solid portion being part of the same single piece.

26. A load-bearing implant according to claim 25, in which the porosity of the porous portion in the region bordering the solid portion is substantially equal to the porosity of the solid portion, the porosity of the porous portion increasing away from the solid portion.

27. A load-bearing implant according to claim 25, in which the solid portion defines a cup which provides part or all of the socket of a ball and socket joint.

28. A load-bearing implant according to claim 27, in which the cup has a concave load bearing cup portion which is solid and the porous portion extends outwardly from the cup portion to a peripheral outer surface.

29. A load-bearing implant according to claim 27, in which the cup is an acetabular cup.

30. A load-bearing implant according to claim 25, in which the solid portion defines a ball which provides part or all of the ball of a ball and socket joint.

31. A load-bearing implant according to claim 30, in which the ball has a convex load bearing ball portion which is solid and the porous portion extends away from the ball portion.

* * * * *